United States Patent [19]

Stednitz

[11] 4,414,966
[45] Nov. 15, 1983

[54] FIXATION PIN
[75] Inventor: Denis P. Stednitz, Redondo Beach, Calif.
[73] Assignee: Ace Orthopedic Manufacturing, Inc., Los Angeles, Calif.
[21] Appl. No.: 252,359
[22] Filed: Apr. 9, 1981
[51] Int. Cl.³ .............................................. A61F 5/04
[52] U.S. Cl. ............................. 128/92 B; 128/92 A
[58] Field of Search .................... 128/92 A, 92 B, 83, 128/84 B, 92 R

[56]        References Cited
        U.S. PATENT DOCUMENTS 2,388,482  11/1945  Haynes ............................. 128/92 A
2,494,229   1/1950  Collison ........................... 128/92 B
3,623,164  11/1971  Bokros ............................. 128/92 B
3,641,590   2/1972  Michelè ........................... 128/92 B
3,741,205   6/1973  Markolp et al. .................. 128/92 B
3,987,499  10/1976  Scharbach et al. ............... 128/92 B
4,312,336   1/1982  Danieletto et al. ............... 128/92 A

OTHER PUBLICATIONS

*Machinery's Handbook*, 20th Edition, by E. Oberg, F. D. Jones and H. L. Horton, pp. 1684–1699.

*Primary Examiner*—C. Fred Rosenbaum
*Assistant Examiner*—C. W. Shedd

[57]                ABSTRACT

A self-cleaning surgical fixation pin having fluted grooves forming self-cleaning knife edges and twin lead helical threads.

7 Claims, 4 Drawing Figures

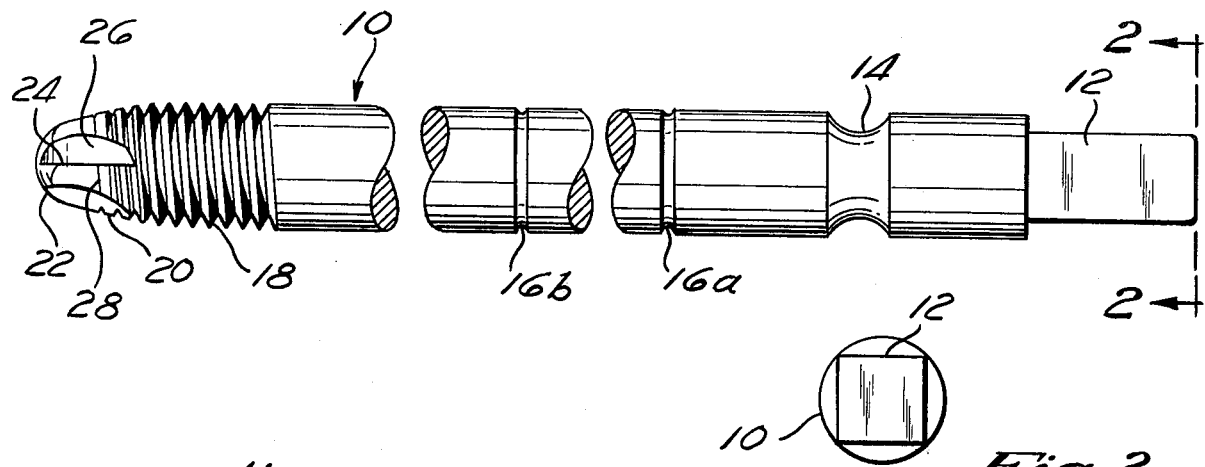
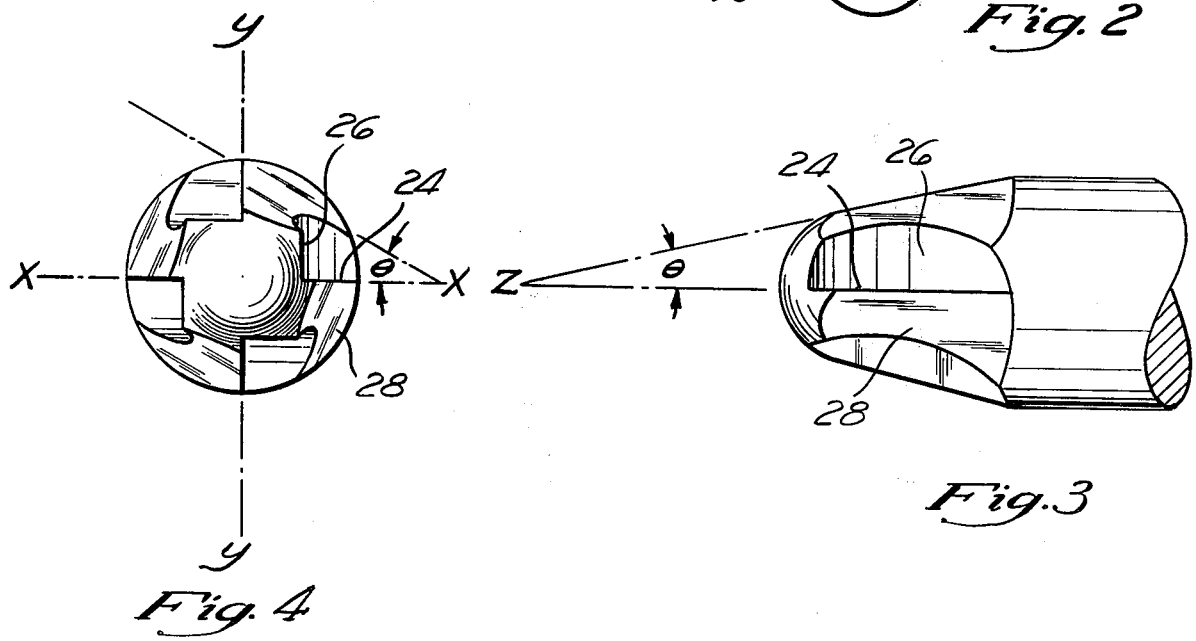

FIXATION PIN

TECHNICAL FIELD

This invention relates to orthopedic surgical devices generally and particularly relates to fixation pins for stabilizing fractures.

BACKGROUND ART

External fixation devices using pins extending into or through bone fragments are generally accepted and widely used throughout the world. The present invention is an improved fixation pin suitable for use with conventional external fixation devices.

Early fixation pins were smooth, cylindrical shafts which were passed through pre-drilled holes. These pins made no screw and thread type engagement to the bone.

Later, pins were developed which were self-drilling and self-tapping. These pins were smooth, cylindrical shafts with the points matched into a pointed spade configuration which formed the dripp tip, having two flat inclined surfaces on opposite sides of the longitudinal axis, and a pointed, wedge-shaped, spade surface with knife edges that scraped away the bone when the shaft was On this self-drilling, self-tapping pin, a self-tapping thread was started at a point approximately halfway up the shallow sloping surfaces. This self-tapping thread continued up the shaft for a distance sufficient to pass through whatever bone the pin was intended for.

The disadvantages of the self-drilling, self-tapping pin were twofold. First, the knife edge of the drill point was not very sharp. Consequently, the drill advanced at a relatively slow speed through the bone. This slow speed was generally slower than the speed with which the self-tapping thread would advance if the hole were pre-drilled before attempting to tap the pin into the bone. This speed differential caused the thread portion to strip out the threads just cut in the bone because of the inability to advance as fast as the self-tapping thread would normally advance.

The second disadvantage was that the relatively slow speed of drilling achieved by this structure resulted in higher temperatures from friction heating of the bone surrounding the hole. Since bone is a living structure, it dies when overheated. Clinical testing has shown that when bone cells are heated to a temperature of about 105° Fahrenheit, they die. As a result, after such a pin was placed in the bone, often a small plug of bone around the hole would subsequently die. As a result, it frequently happened that a small plug of bone with the pin attached would fall out. New and painful treatment was thus necessitated for the patient.

Self-penetrating and pre-drilled screws are known. The self-penetrating types generally have a sharp point on the tip of the screw similar to self-penetrating wood screws. These self-penetrating screw structures could not be used in orthopedic work because the hardness and thickness of the bone portion surrounding the marrow would not permit the screw to penetrate absent a drilling point on the tip of the screw.

In fixing a broken bone with a fixation pin the orthopedic surgeon must pass a fixation pin through the bone table on one side of the marrow, pass the pin through the marrow and then must find the hole in the bone table on the other side of the marrow with the tip of the pin. All these procedures must be done by feel with the physician unable to see the holes drilled in the bone. Since the interior surfaces of the bone table facing the marrow tend to be porous, if a sharp point were used on the fixation pin, finding the hole in the bone table on the far side of the marrow would be more difficult because of the difficulty of sliding a sharp point over a porous surface. Generally pre-drilled type, self-tapping screws utilize truncated conical surfaces at their points. These truncated surfaces have sharp edges which could catch on the porous internal bone surfaces facing the marrow when attempting to slide the fixation pin over the surface in search of the far-side hole.

In addition, such pre-drilled, self-tapping screws generally utilize only one flute cut in the tip to give a cutting edge to the helical rib of the thread. Where only one flute is used, there are unbalanced cutting forces generated as the helical rib cuts a helical groove in the bone. These forces would create very large pressures pressing the screw shaft against the bone at a point diagonally opposite the flute. These large pressures could cause damage to the bone material. Hence, the use of a structure causing balanced cutting forces is preferable.

SUMMARY OF THE INVENTION

The present invention, in its exemplary and preferred form, is an orthopedic fixation pin which is adapted to be threadably attached, adjacent the distal end thereof, with a bone of the user patient, and to be attached to a fixation frame, of any desired type, adjacent to the proximal end thereof. The pin comprises an elongate cylindrical shaft having threads formed at the distal end thereof for attachment to the bone. The threaded distal end of the pin comprises a symmetrical dull tip portion which has a maximum diameter less than the diameter of the shaft, i.e., there is a transition portion of increasing diameter between the tip portion and the shaft. Threads are formed on the pin from the tip portion, through the transition portion, and, if desired, onto the shaft to the pin, adjacent the transition portion, for a desired diatance along the shaft. Self-tapping, self-cleaning, cutting edges of the thread are formed on the distal end of the shaft by means of at least two flutes formed in the tip and transition portions, and if desired, extending into the shaft portion. Each of the flutes is defined by first and second surfaces. The first surface of the flute is generally planar and lies substantially in coincident with a radius of the shaft, i.e., the plane of the first surface lies on a diameter of the shaft, or lies at least substantially in the plane of the diameter of the shaft. The outer periphery of the first surface is defined by the intersection of the first surface with the tip portion, transition portion, and, optionally, with the shaft portion, if the first surface extends longitudinally from the tip end to the shaft portion. The other edge of the first surface is defined by the intersection thereof with the second surface. Generally, the first surface and the second surface are substantially coextensive and extend from proximate the distal end of the transition portion, typically between the distal end of the transition portion and the tip of the pin, to proximate the proximal end of the transition portion, although the surface may extend into the shaft portion of the pin, if desired.

The second surface is longitudinally generally coextensive with the first surface and curves from a portion of the surface which is coincident with a chord lying slightly displaced from the center of the shaft, the curving surface extending outwardly, as it extends longitudinally in the direction of the proximal end of the shaft, to terminate at a tangent to the shaft. The second surface is conveniently, and preferably, a radius cut, the surface defining longitudinally a portion of a circular surface, but other cut configurations may be used.

The flutes are substantially symmetrically arranged about the axis of the shaft, and are so configured and constructed as to form non-fluted spaces between the respective flutes. In the preferred embodiments, which are shown in the exemplary drawings, there are four flutes and four non-fluted spaces therebetween. The non-fluted surfaces between the flutes are substantially flat and intersect the first surface of the flute adjacent thereto to form a cutting edge in the form of the thread configuration, thereby resulting in a self-tapping cutting edge for the threads on the distal end of the pin.

The transition portion is preferably, but not necessarily, in the form of a frustocone extending with decreasing diameter from the shaft portion to the tip portion. The flutes and non-fluted surfaces therebetween are formed generally in the region of the frustoconical transition zone, although the flutes can extend beyond the transition zone.

BRIEF DESCRIPTION OF THE DRAWINGS

FIG. 1 is a plan view of the orthopedic fixation pin of this invention.

FIG. 2 is an end view taken along lines 2—2 of FIG. 1 showing the proximal or chuck end of the pin.

FIG. 3 is an enlarged side view of the tip of a pin during manufacture before being threaded.

FIG. 4 is an end view showing the tip and transition portions of the unthreaded pin of FIG. 3.

BEST MODE FOR CARRYING OUT THE INVENTION

FIG. 1 depicts the overall pin of this invention. The pin 10 comprises a proximal end on which a drive portion 12, adapted to be fitted into a driving chuck, is formed. The driving portion 12, as shown in FIG. 2, is preferably square but, of course, can be any desired configuration, even round, if the chuck is adapted to grasp a round driving portion. Since it is usually desirable to be able to withdraw the pin while rotating it, a groove 14 is formed adjacent to proximal end of the pin. This groove is adapted to be received in conventional drilling equipment so as to permit application of withdrawal force, to the right as shown in FIG. 1, by the chuck while rotating the pin. In addition, a desired number of measuring markers 16a, 16b, and other such markers not shown, may be included. Typically, these measuring markers are spaced at one centimeter intervals along the length of the shaft to permit the surgeon to determine the distance of penetration of the pin.

The pin itself is simply a longitudinal cylindrical shaft. The distal end of the shaft 10 is threaded, as shown generally at 18, and includes a transition portion 20 between the shaft portion on which threads 18 are shown and a tip portion 22. At least two, and in the preferred embodiment, four flutes are formed in the transition portion and extending into the tip portion and the shaft portion, if desired. Each of the flutes is formed by two surfaces shown at 24 and 26. The flutes are symmetrically placed about the center axis of the shaft and form, in the spaces between the flutes, non-fluted surfaces 28.

The construction of the tip and transition portions are the significant features of this invention and are best understood by reference to FIGS. 3 and 4, which show a shaft 10 before being threaded, but with the flutes and non-fluted surfaces, as well as a transition portion 20, already formed. The transition portion 20 is conveniently in the form of a frustocone having a maximum diameter corresponding to the diameter of the shaft and diminishing to the maximum diameter of a tip portion 22 which, in the exemplary embodiment, is in the configuration of a portion of a spherical surface.

While the manufacturing steps may be carried out in any number of sequences, it is convenient to consider the configuration of the tip by selecting an arbitrary sequence of steps in the manufacture and considering the structure resulting from each of the steps. Thus, if one considers the manufacture of the distal end of the shaft starting with a plane cylindrical shaft with a square end, the following steps may be considered as occurring during manufacture. First, one may form the transition zone 20 simply by forming a frustoconical portion on the end of the shaft. Following manufacture, only a small portion of this frustoconical transition portion remains, as indicated in FIG. 3. It is convenient to consider the next step as forming the intersecting surfaces 24 and 26. Looking at FIG. 3, a single end mill cut along a circular arc, the circular arc defining the surface 26, and the end of the cut defining the surface 24, results in the formation of one flute. This manufacturing step is repeated one more time, or two or three more times, depending upon the number of flutes desired. In the exemplary preferred embodiment, four symmetrically spaced flutes are formed. Between each of the flutes there remains a non-fluted surface. In the exemplary embodiment, though not necessary to the invention, these non-fluted surfaces are flattened, using any conventional milling device, and so configured as to intersect the surface 24 of the flute, the intersection between the surface 24 and the flattened surface 28 constituting a self-tapping cutting edge for the threads on the pin. The surface 28 need not be flat and may terminate just short of intersecting with the surface 24 to leave a slight trailing surface behind the cutting edge. Finally, the tip portion of the pin is formed by simply machining the tip into a partial hemispheric configuration, or any dull configuration. The tip extremity may even be flat. The exact configuration of the tip is not critical, so long as it is not so sharp as to prevent relatively free movement of the pin along the surface of the bone.

Specific angles are not critical to the invention, but in the best mode which is exemplified in the drawing, the transition portion is formed in the shape of a frustocone having a frustoconical surface lying at an angle $\theta$ which is about eight degrees measured from the longitudinal Z axis of the pin shaft. The angle may vary considerably without departing from the invention, by an angle of about eight to ten degrees has been found quite satisfactory. The angle, of course, is measured using the axis or the cylindrical surface of the shaft as the reference. The surface 28 is preferably formed at an angle of about seventy degrees with the plane of the surface 24 which it intersects. The angle is, of course, not especially critical as any angle from about twenty to forty degrees could readily be used. An angle of about thirty degrees has been found to be satisfactory where surface 28 intersects surface 24, as measured from the X-axis, best shown in FIG. 4.

FIG. 3 best depicts the relationship of the flutes to the end portion and the transition portion. In the preferred embodiment, the flute extends from proximate the distal end of the transition portion, and preferably between the distal end of the transition portion and the tip end of the pin, longitudinally toward the distal end of the pin to about the distal end of the transition portion. In the exemplary embodiment, the flutes do not extend into the shaft portion of the pin but the flutes could readily be designed to extend into the shaft of the pin without detriment, but also without significant benefit, to the design of the self-tapping screw which results when the shaft is threaded.

Surgical pins may be made in various sizes, depending upon the size of the bone, to which the surgical fixation pin is to be attached, and the strength and rigidity required in a particular application. A very useful size of orthopedic fixation pin is described hereafter, but it will be understood that this is simply to exemplify the best embodiment of the invention, and that these dimensions have no particular criticality or significance insofar as the inventive concept is concerned. The pin shaft, in an exemplary embodiment, is about 0.157 inch, the maximum diameter of the end portion, which is preferably in the form of a sphere, sometimes called the root diameter, is about 0.121 inch, the transition portion extending about 0.09 inch between the maximum diameter of the spherical end portion and the full diameter of the shaft.

While the particular angles of the surfaces are not critical per se, it is important for maximum benefit that the surface form a clearance space behind the cutting edge to permit small bone fragments following the cutting edge to float freely and to the next flute. Thus, these small bone fragments should not become pinched between the transition surface and the periphery of the hole, and thus damage or destroy the thread configuration or tend to cause binding during the threading operation.

Any convenient threading arrangement may be used but, in the preferred exemplary embodiment, a twin lead thread arrangement is utilized. Twin lead threading involves two spiral threads superimposed upon one another, the two threads starting on opposite sides of the shaft. Twin lead threads are well-known and standard threading dyes may be used. The threads may, of course, be cut to any pitch or coarseness desired, and there is no particular criticality as to the threading utilized.

The surgical fixation pins described may be manufactured of any biologically compatible material which is sufficiently strong and rigid to provide adequate support and sufficiently hard to permit tapping of threads into the bone. In the preferred embodiment, the pins are manufactured of titanium alloy containing about ninety percent titanium, six percent aluminum and four percent vanadium. The pins may also be manufactured from 316 stainless steel.

In using the pin of this invention, any fixation device, such as that invented by Dr. Fischer depicted and referred to U.S. patent application Ser. No. 85,996, Filed Oct. 18, 1979, or the conventional Hoffmann fixation device, may be used in conjunction with the surgical pins of this invention. In using these surgical pins, a drill but substantially the same diameter as the root diameter of the pin is used to pre-drill a hole in the bone. Generally, the drill bit with straight flute has been found to be superior to conventional spiral flute drill bits, since the spiral flute drill tends to create a butterfly shaped chip on the back of the bone as it emerges. There is no particular criticality, however, to the drill bit used, and any conventional surgical drill bit having a hole diameter approximating the root diameter of the pin may be used.

INDUSTRIAL APPLICATION

This invention finds application in orthopedic surgery in the fixation of broken bones generally, and particularly in the fixation of fractures of the limbs.

It will be understood that the foregoing specification describes an exemplary embodiment of the invention and that variations may be made in dimension, general appearance and configuration, without departing from the scope of the invention as defined in the following claims:

What is claimed is:

1. In an orthopedic fixation pin adapted to be threadably attached adjacent the distal end with a bone of the user patient and to be attached to a fixation frame adjacent the proximal end thereof, the pin comprising an elongate cylindrical shaft having threads formed at the distal end thereof for attachment to the bone, the improvement wherein the threaded distal end of the pin comprises;
   a symmetrical hemispherical dull tip portion having a maximum diameter less than the diameter of the shaft;
   a transition portion of increasing diameter between the tip portion and the shaft;
   threads formed on the pin from the tip portion through the transition portion and onto the shaft adjacent the transition portion;
   at least two flutes formed in the tip and transition portions, each of said flutes being defined by first and second surfaces, the first surface being generally planar and lying substantially in coincidence with a radius of the shaft and extending longitudinally from proximate the distal end of the transition portion to proximate the proximal end of the transition portion of the pin, the second surface being longitudinally generally coextensive with the first surface and curving from a surface coincident to a chord proximate the center of the shaft outwardly to terminate at a tangent to the shaft, the flutes being substantially symmetrically arranged about the axis of the shaft and so configured and constructed as to form non-fluted spaces therebetween;
   the non-fluted surfaces between the flutes being substantially flat to form a self-tapping cutting edge for the threads on the pin.

2. The fixation pin of claim 1 wherein the substantially flat non-fluted surface forming the self-tapping cutting edge lies in a plane which intersects the first surface of the flute at an angle of between twenty and seventy degrees elevation.

3. The fixation pin of claim 1 wherein the transition portion is formed in the shape of a frusto conical surface lying at an angle of between eight to ten degrees elevation from the longitudinal center axis of the cylindrical shaft.

4. A self-tapping, self-cleaning threaded orthopedic fixation pin for use in a pre-drilled bore in a bone, comprising:
   an elongate shaft having a proximal end adapted to be received by a chuck and a distal end threaded to be screwed into the bone;

the distal end comprising a generally hemispherical tip portion having a maximum diameter less than the shaft diameter and a distal tip substantially on the longitudinal centerline of said pin, a tapering transition section between the tip portion and the shaft, at least two equally spaced flutes extending from proximate said distal tip, across said transition section, and at least to the main shaft portion; each flute comprising the intersection of a first surface and a second surface and forming a space to collect bone fragments formed during tapping of the bone and having a self-tapping cutting edge for forming threads in the bone;

each cutting edge comprising the intersection of the first surface with a planar third surface formed on the transition surface between each of the flutes.

5. An orthopedic fixation pin comprising:

a shaft having a proximal end for being received in a chuck for rotatably driving the pin, a central shaft portion, a hemispherical distal dull tip portion, and a transition portion between the distal dull tip portion and the central shaft portion, threads formed on the distal end of the shaft from the distal dull tip portion to at least the distal end of the central shaft portion, a plurality of symmetrically disposed and spaced flutes in the distal tip and transition portions, each such flute forming a chip receiving space, and non-fluted surfaces between the spaced flutes which form a self-tapping cutting edge for forming threads in a bone fragment.

6. The fixation pin of claim 5 wherein the distal dull tip portion is generally hemispherical in configuration.

7. The fixation pin of claims 5 or 6 wherein the cutting edge is formed by the intersection of one surface forming the flute and a generally flat surface formed in the non-fluted surfaces between the flutes.

* * * * *